United States Patent [19]

Cerami et al.

[11] Patent Number: 5,128,122
[45] Date of Patent: Jul. 7, 1992

[54] METHOD AND AGENTS FOR PREVENTING STAINING OF TEETH

[75] Inventors: Anthony Cerami, Shelter Island; Michael A. Yamin, Tappan, both of N.Y.

[73] Assignee: The Rockefeller University, New York, N.Y.

[21] Appl. No.: 604,820

[22] Filed: Oct. 26, 1990

Related U.S. Application Data

[63] Continuation of Ser. No. 290,938, Jan. 4, 1989, abandoned, and a continuation-in-part of Ser. No. 264,930, Nov. 2, 1988, Pat. No. 4,983,604, which is a continuation-in-part of Ser. No. 119,958, Nov. 13, 1987, Pat. No. 4,908,446, said Ser. No. 290,938, is a continuation-in-part of Ser. No. 149,726, Jan. 29, 1988, Pat. No. 4,978,684, which is a continuation-in-part of Ser. No. 119,958, Nov. 13, 1987, Pat. No. 4,908,446, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^5$ .................................. A61K 7/16
[52] U.S. Cl. ......................... 424/49; 433/216; 424/50; 424/51; 424/52; 424/53; 424/54
[58] Field of Search ................... 433/216; 424/49–54

[56] References Cited

U.S. PATENT DOCUMENTS 4,908,446  3/1990  Ulrich et al. .................... 540/553
4,978,684  12/1990 Cerami et al. .................... 514/632

Primary Examiner—Ronald W. Griffin
Attorney, Agent, or Firm—Klauber & Jackson

[57] ABSTRACT

The present invention relates to methods and agents for preventing the staining of teeth caused by the nonenzymatic browning of proteins in the oral cavity. Both oral and parenteral administration ft the agents are disclosed. Suitable agents for the inhibition of nonenzymatic browning may be formulated as rinses and toothpastes, and include compounds capable of reacting with the carbonyl moiety of the early glycosylation product resulting from the initial reaction of a target protein in the nonenzymatic browning reaction. Preferred agents are those having an active nitrogen-containing substituent, as well as amino acids, their esters and amides. These preparations may further include known antiplaque agents such as chlorhexidine.

26 Claims, 1 Drawing Sheet

METHOD AND AGENTS FOR PREVENTING STAINING OF TEETH

This invention was made in part with government support under Grant Number PHS AM 19655 awarded by the National Institutes of Health. The government has certain rights in the invention.

CROSS REFERENCE TO RELATED APPLICATIONS

This is a Continuation of application Ser. No. 07/290,938, filed Jan. 4, 1989, now abandoned, which is a Continuation-in-Part of copending application Ser. No. 149,726, filed Jan. 29, 1988, now U.S. Pat. No. 4,978,684, which is a Continuation-in-Part of copending application Ser. No. 119,958, filed Nov. 13, 1987, now U.S. Pat. No. 4,908,446, which is a Continuation-in-Part of copending application Ser. No. 798,032, filed Nov. 14, 1985, now U.S. Pat. No. 4,758,583, which is a Continuation-in-Part of application Ser. No. 590,820, filed Mar. 19, 1984 and now U.S. Pat. No. 4,665,192, issued May 12, 1987, by Anthony Cerami. The present application is also a Continuation-in-Part of copending application Ser. No. 264,930, filed Nov. 2, 1988, now U.S. Pat. No. 4,983,604, which is a Continuation-in-Part of the aforementioned Ser. No. 119,958.

RELATED PUBLICATIONS

The Applicants are co-authors of the following articles directed to the subject matter of the present invention: "COVALENT ATTACHMENT OF SOLUBLE PROTEINS BY NONENZYMATICALLY GLYCOSYLATED COLLAGEN: ROLE IN THE IN SITU FORMATION OF IMMUNE COMPLEXES", Brownlee M., Pongor S., Cerami A., (1983), *J. Exp. Med.*, 158, pp. 1730-1744; and "AGING OF PROTEINS: ISOLATION AND IDENTIFICATION OF FLUORESCENT CHROMOPHORE FROM THE REACTION OF POLYPEPTIDES WITH GLUCOSE", Pongor, et al, *Proc. Natl. Acad. Sci. USA*, 81, pp. 2684-2688, (May, 1984), both of which are incorporated herein by reference.

BACKGROUND OF THE INVENTION

The present invention relates generally to the reaction that occurs between glucose and proteins, and more particularly to the inhibition by various aminoguanidine derivatives of the reaction of nonenzymatically glycosylated proteins leading to advanced glycosylation end products.

The nonenzymatic browning reaction which occurs in the oral cavity results in the discoloration of teeth. Presently used anti-plaque agents accelerate this nonenzymatic browning reaction and further the staining of the teeth.

The appeal of a perfect smile composed of pearly-white teeth is undeniable. Many dollars are spent to achieve this appearance, and the natural discoloration which occurs on the tooth surfaces often becomes quite noticeable in many individuals. Tooth discoloration is also greatly accelerated in most individuals who use certain anti-plaque agents to prevent oral disease. The purpose of the present invention is to provide a method and agents for preventing the discoloration which occurs on the tooth surface as a result of nonenzymatic browning, both naturally and as a result of the use of anti-plaque agents. As used herein, "tooth" and "teeth" refer to both naturally occurring and artificial teeth, artificial tooth surfaces and restorations.

Dental caries, gingivitis and periodontal disease are widespread and affect nearly all individuals to some extent cosmetically, medically, and financially. These conditions arise from the action of certain microorganisms, principally bacteria, which colonize surfaces in the mouth and whose action lead to demineralization of bone, resulting in caries, and chronic irritation and infection of gum tissue (gingivitis) especially in pockets surrounding the teeth, leading to periodontal disease. The results of both processes can be painful, disfiguring and psychologically debilitating.

The development of tooth and gum disease is a complex process involving contributions from the tooth and gum surface, components and properties of saliva, diet, and the numerous species of bacteria present in the mouth, as well as many other factors. Generally, incubation of a newly cleaned tooth surface in the mouth initially results in the deposition on the surface of a material called pellicle, which is composed of protein and polysaccharide derived from saliva and bacterial cells. As colonizing bacteria grow, they produce a polysaccharide from the decomposition of food sugars. This polysaccharide favors the attachment of the bacteria to the tooth surface and also favors mineralization of calcium salts from saliva in the pellicle. As the process continues, the bacterial mass known as plaque becomes a focus for demineralization of bone and irritation of tissues. Acids produced by bacteria during food sugar fermentation dissolve bone, and the plaque mass prevents buffers in saliva from neutralizing these acids. The result is dental caries. The bacteria in plaque and those residing in pockets surrounding teeth produce endotoxin and other well-known bacterial products which are intensely irritating to tissues and cause the tissues to react, resulting in recession of gum tissue, demineralization of bone, and localized irritation.

One of the consequences of long-term exposure of proteins in the pellicle and plaque to sugars in the mouth is the process of nonenzymatic browning, which results in discoloration of the tooth surface. Nonenzymatic browning, also known as the Maillard reaction, has been well studied by food chemists since it is responsible for the brown color which forms during the cooking and long-term storage of foods. In this reaction, amino groups in food proteins and other molecules react with sugars in food proteins and other molecules react with sugars to form covalent adducts which undergo rearrangements and result in highly polymerized, colored products. While this process is well-known in food, only recently was its significance realized as concerns the human body and consequences of the long-term exposure of glucose to amino groups on proteins and other macromolecules in the body. The Maillard reaction in vivo has been studied extensively in the last few years and nonenzymatic browning and cross-linking of proteins in vivo has been shown to be an important mechanism by which the sequelae of diabetes and aging arise (see M. Brownlee et al., "Nonenzymatic glycosylation and the pathogenesis of diabetic complications," *Annals of Internal Medicine*, 101, pp. 527-537 (1986)). Elevate glucose levels in diabetes leads more rapidly to consequences involving permanent cross-linking of proteins, yet the normal glucose levels in nondiabetics eventually leads to the same complications.

Methods to prevent nonenzymatic browning in vivo with agents such as aminoguanidine and other inhibitors have been studied (Brownlee et al., "Aminoguanidine prevents diabetes-induced arterial wall protein cross-linking," *Science,* 232, pp. 1629-1632 (1986)), Cerami et al., U.S. patent application Ser. No. 798,032; and U.S. patent application Ser. No. 07/119,958.

For many years certain agents have been tested and used to reduce the extent of oral diseases including dental caries, gingivitis and periodontal disease. Regular brushing and flossing apparently are inadequate, at least to the extent practiced by the average individual. Abrasive agents such as silica have been incorporated into toothpastes to attempt to physically remove plaque by enhancing the effectiveness of brushing. Antimicrobial agents have been formulated in oral rinses for regular use to kill bacteria in the mouth. Such agents include sanguinarine, an extract from the bloodroot, which kills certain oral bacteria; certain forms of active peroxide for killing microorganisms; rinses containing alcohol and other ingredients and, more recently, a class of cationic anti-microbial agents with remarkable anti-plaque properties.

These latter agents, the cationic antiseptics, include such agents as alexidine, cetyl pyridinium chloride, chlorhexidine gluconate, hexetidine, and benzalkonium chloride. Many have been tested for efficacy but one, chlorhexidine gluconate, has shown the greatest promise as an anti-plaque agent of low toxicity (see Hull, "Chemical Inhibition of Plaque," *J. Clin. Periodontol.,* 7, pp. 431-432 (1980); Bain, "Chlorhexidine in Dentistry: A Review," *New England Dent. J.,* 76, pp. 49-54 (1980); Tonelli et al., "Chlorhexidine: A Review of the Literature," *J. West. Soc. Periodent.,* 31, pp. 5-10 (1983), and has recently become available in the United States in a prescription formulation known as Periodex ® which contains a 0.12% chlorhexidine gluconate in a solution of water, alcohol, glycerine, flavoring, sweetening and coloring agents. Chlorhexidine gluconate, formulated in such a rinse, shows excellent promise as an anti-plaque agent, but it has been found to possess an unfortunate side effect: staining of teeth. While this side effect is of no medical concern, it is an extreme psychologic concern because stained teeth look ugly and project an undesirable image to others.

Tooth staining by chlorhexidine and other anti-plaque agents apparently results from the enhancement of the Maillard reaction. Nordbo, *J. Dent. Res.,* 58, p. 1429 (1979) reported that chlorhexidine and benzalkonium chloride catalyze browning reactions in vitro. Chlorhexidine added to mixtures containing sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products. Thus, there exists a need for preventing the staining caused by chlorhexidine gluconate and other cationic mouth rinses which will not interfere with their potent antimicrobial and resulting anti-plaque activity.

SUMMARY OF THE INVENTION

In accordance with the present invention, a method of preventing the staining of teeth caused by the nonenzymatic browning of proteins in the oral cavity is disclosed. In particular, agents for the inhibition of nonenzymatic browning are formulated as rinses and toothpaste alone or in combination with known antiplaque agents such as chlorhexidine. Additionally, the agent can be administered orally or parenterally since it concentrates in the salivary glands and is subsequently secreted into the oral cavity in the saliva.

The agents which can be utilized in the methods and formulations of this invention are those disclosed in our co-pending applications Ser. No. 264,930, filed Nov. 12, 1988, Ser. No. 798,032, filed Nov. 14, 1985, and Ser. No. 119,958, filed Nov. 13, 1987, herein incorporated by reference. Thus, the agents are those capable of reacting with the carbonyl moiety of the early glycosylation product formed by the initial glycosylation of the target protein in the nonenzymatic browning reaction. Preferred agents are those having an active nitrogen-containing substituent. Among these are those wherein the active nitrogen substituent is a hydrazine group. Others are amino acids and their esters and amides.

Specific agents utilizable in the present invention are aminoguanidine, α-hydrazinohistidine, lysine and the substituted aminoguanidine derivatives having the structural formula wherein R is a group of the formula and $R^1$ is hydrogen or a lower alkyl group of 1-6 carbon atoms, a hydroxyethyl group, or together with $R_2$ may be a lower alkylene bridge of 2-4 carbon atoms;

$R_2$ is hydrogen or a lower alkyl group of 1-6 carbon atoms or together with $R_1$ or $R_3$ is a lower alkylene bridge of 2-4 carbon atoms, amino, hydroxy, or an aminoalkylene group of the formula wherein n is an integer of 2-7 and $R_6$ and $R_7$ are independently a lower alkyl group of 1-6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring;

$R_3$ is hydrogen, a lower alkyl group of 1-6 carbon atoms, or together with $R_2$ or $R_4$ is a lower alkylene bridge of 2-4 carbon atoms;

$R_4$ is hydrogen, a lower alkyl group of 1-6 carbon atoms or together with $R_3$ is a lower alkylene bridge of 2-4 carbon atoms; or an amino group;

$R_5$ is hydrogen, or a lower alkyl group of 1–6 carbon atoms;

with the proviso that at least one of $R_1$, $R_2$, $R_3$, $R_4$ or $R_5$ is other than hydrogen; or R is an acyl or a lower alkylsulfonyl group of up to ten carbon atoms and $R_1$ is hydrogen;

and their pharmaceutically acceptable acid addition salts.

Certain of the compounds of formula I are represented by the formula II (II)

wherein $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring.

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_2$, $R_3$, $R_4$ or $R_5$ is other than hydrogen;

and their pharmaceutically acceptable acid addition salts.

Thus, certain of the compounds of this invention are substituted aminoguanidine derivatives.

Certain of the aminoguanidine derivatives useful in the method of the present invention are novel compounds. Correspondingly, the present invention relates to these novel compounds, as well as to their methods. Certain of these novel compounds are represented by the formula III (III)

wherein $R_8$ is amino, hydrogen, 2-hydroxylethyl or lower alkyl, $R_9$ and $R_{10}$ are hydrogen, 2-hydroxylethyl, or a lower alkyl group and m is an integer of 2–4. Certain compounds of this group are also represented by the formula (IV)

wherein $R_{11}$, $R_{12}$ and $R_{13}$ are hydrogen or a lower alkyl group and m is an integer of 2–4.

Specifically preferred compounds are those wherein $R_8$, $R_9$ and $R_{10}$ are all hydrogen and those wherein m=2.

Other novel compounds of this invention are those compounds of formula II wherein $R_6$ and $R_7$ together with the nitrogen atom are a morpholino group. These are thus represented by the formula wherein

$R_1$ is hydrogen or a lower alkyl group of 1–6 carbon atoms; a hydroxyethyl group, n is an integer of 2–7;

$R_3$ is hydrogen, a lower alkyl group of 1–6 carbon atoms, or together with $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; with the proviso that at least one of $R_1$, $R_3$, $R_4$ or $R_5$ is other than hydrogen; and their pharmaceutically acceptable acid addition salts.

Also novel are the group of compounds of formula II where $R_1$ is a hydroxyethyl group. These are thus represented by the formula wherein $R_2$ is hydrogen or a lower alkyl group of 1–6 carbon atoms or together with $R_3$ is a lower alkylene bridge of 2–4 carbon atoms, amino, hydroxy or an aminoalkylene group of the formula wherein n is an integer of 2–7 and $R_6$ and $R_7$ are independently a lower alkyl group of 1–6 carbon atoms or together with the nitrogen atom are a morpholino or piperidino group;

$R_3$ is hydrogen, a lower alkyl group of 1–6 carbon atoms, or together with $R_2$ or $R_4$ is a lower alkylene bridge of 2–4 carbon atoms;

$R_4$ is hydrogen, a lower alkyl group of 1–6 carbon atoms or together with $R_3$ is a lower alkylene bridge of 2–4 carbon atoms; or an amino group;

$R_5$ is hydrogen, or a lower alkyl group of 1–6 carbon atoms; and their pharmaceutically acceptable acid addition salts.

The compounds of this invention appear to react with the glycosylation product thereby preventing the same from later forming the advanced glycosylation end products of nonenzymatic browning which result in the discoloration of the teeth in the oral cavity.

Accordingly, it is a principal object of the present invention to provide a method of inhibiting the discoloration of teeth resulting from nonenzymatic browning in the oral cavity which comprises administration to a subject in need of such therapy an amount effective to inhibit the formation of advanced glycosylation end products of a composition comprising an agent capable of reacting with the carbonyl moiety of the early glycosylation product formed by the initial glycosylation in the nonenzymatic browning reaction.

It is a further object of the present invention to provide agents capable of participating in the reaction with the said early glycosylation products in the method as aforesaid.

It is a still further object of the present invention to provide compositions incorporating agents capable of participating in the reaction with the said early glycosylation products adapted for use in the oral cavity according to the aforesaid method.

Other objects and advantages will become apparent to those skilled in the art from a consideration of the ensuing description which proceeds with reference to the following illustrative drawings.

DETAILED DESCRIPTION OF THE PREFERRED EMBODIMENTS

In accordance with the present invention, methods and associated compositions have been developed which are believed to inhibit the discoloration of teeth resulting from nonenzymatic browning in the oral cavity. In particular, the invention relates to a method of inhibiting the discoloration of teeth resulting from nonenzymatic browning in the oral cavity which comprises administration to a subject in need of such therapy an amount effective to inhibit the formation of advanced glycosylation end products of a composition comprising an agent capable of reacting with the carbonyl moiety of the early glycosylation product formed by the initial glycosylation in the nonenzymatic browning reaction.

In accordance with this method, the agents capable of reacting with the carbonyl moiety of the early glycosylation product formed by the initial glycosylation in the nonenzymatic browning reaction are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent capable of reaction with the carbonyl moiety of the early glycosylation product formed by the initial glycosylation in the nonenzymatic browning reaction is formulated in compositions in an amount effective to inhibit the formation of advanced glycosylation end products. This amount will, of course, vary with the particular agent being utilized, but typically is in the range of 0.01% to 1.0%, by weight, of the particular formulation.

Additionally, since the agents of the aforesaid method are concentrated in the salivary glands upon oral ingestion or parenteral administration, they can be so administered. This concentration in the salivary glands results in their secretion into saliva, the net result being that they are functionally placed in the oral cavity where they can effect their desired method. For such administration, the particular agent can be formulated in any conventional oral or parenteral dosage form. A particularly desirable dosage form is the incorporation of the agent into a vitamin tablet or fluoride tablet so as to maximize patient, and particularly juvenile patient, compliance.

Specific agents utilizable in the present invention are aminoguanidine, α-hydrazinohistidine, lysine and the aminoguanidine derivatives encompassed by the formula (I)

wherein R is a group of the formula and $R_1$ is hydrogen or a lower alkyl group of 1–6 carbon atoms, a hydroxyethyl group, or together with $R_2$ may be a lower alkylene bridge of 2–4 carbon atoms;

$R_2$ is hydrogen or a lower alkyl group of 1–6 carbon atoms or together with $R_1$ or $R_3$ is a lower alkylene bridge of 2–4 carbon atoms, amino, hydroxy, or an aminoalkylene group of the formula wherein n is an integer of 2-7 and $R_6$ and $R_7$ are independently a lower alkyl group of 1-6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring.

$R_3$ is hydrogen, a lower alkyl group of 1-6 carbon atoms, or together with $R_2$ or $R_4$ is a lower alkylene bridge of 2-4 carbon atoms;

$R_4$ is hydrogen, a lower alkyl group of 1-6 carbon atoms or together with $R_3$ is a lower alkylene bridge of 2-4 carbon atoms; or an amino group;

$R_5$ is hydrogen, or a lower alkyl group of 1-6 carbon atoms; with the proviso that at least one of $R_1$, $R_2$, $R_3$, $R_4$ or $R_5$ is other than hydrogen; or R is an acyl or a lower alkylsulfonyl group of up to ten carbon atoms and $R_1$ is hydrogen;

and their pharmaceutically acceptable acid addition salts.

Other agents utilizable in the present invention are those of the formula wherein $R_1$ is hydrogen or a lower alkyl group of 1-6 carbon atoms, a hydroxyethyl group, or together with $R_2$ may be a lower alkylene bridge of 2-4 carbon atoms;

$R_2$ is hydrogen or a lower alkyl group of 1-6 carbon atoms or together with $R_1$ or $R_3$ is a lower alkylene bridge of 2-4 carbon atoms, amino, hydroxy, or an aminoalkylene group of the formula wherein n is an integer of 2-7 and $R_6$ and $R_7$ are independently a lower alkyl group of 1-6 carbon atoms or together with the nitrogen atom are a morpholino or piperidino group;

$R_3$ is hydrogen, a lower alkyl group of 1-6 carbon atoms, or together with $R_2$ or $R_4$ is a lower alkylene bridge of 2-4 carbon atoms;

$R_4$ is hydrogen, a lower alkyl group of 1-6 carbon atoms or together with $R_3$ is a lower alkylene bridge of 2-4 carbon atoms; or an amino group;

$R_5$ is hydrogen, or a lower alkyl group of 1-6 carbon atoms;

with the proviso that at least one of $R_1$, $R_2$, $R_3$, $R_4$ or $R_5$ is other than hydrogen;

and their pharmaceutically acceptable acid addition salts.

The lower alkyl and lower alkoxy groups referred to herein contain 1-6 carbon atoms and include methyl, methoxy, ethyl, ethoxy, propyl, propoxy, butyl, butoxy, pentyl, pentyloxy, hexyl, hexyloxy and the corresponding branched chain isomers thereof.

The acyl radicals referred to herein are residues of lower alkyl, aryl and heteroaryl carboxylic acids containing 2-10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group, e.g., glutaryl or succinyl. The heteroaryl groups referred to above encompass aromatic heterocyclic groups containing 3-6 carbon atoms and one or more heteroatoms such as oxygen, nitrogen or sulfur.

The lower alkyl sulfonyl groups of the compounds of this invention are those containing from 1 to 7 carbon atoms and are typified by methylsulfonyl, ethylsulfonyl, n-propylsulfonyl, tbutylsulfonyl and the like.

The term "aryl" as used herein refers to phenyl and lower alkyl substituted phenyl groups containing 6-10 carbon atoms and substituted by one or more substituent groups selected from among chloro, bromo, fluoro, carboxy, lower alkyl, hydroxy, or lower monoalkylamino, lower dialkylamino, lower alkoxy.

The compounds are capable of inhibiting the formation of advanced glycosylation end products on such target proteins, by reacting with the carbonyl moiety of the early glycosylation product that is formed by the initial glycosylation of the protein.

It is the carbonyl group located near the junction between sugar and protein segments of the early glycosylation product that is theorized to comprise an active site that causes the further cross-linking of the protein to form the advanced glycosylation end product. Thus, the reaction of the compounds of this invention with this carbonyl moiety is believed to inhibit the late stage Maillard effect.

Since the composition of the present invention is utilized for in vivo or therapeutic purposes, it is to be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a compound may be converted to the hydrochloride salt from the commercially available bicarbonate salt to improve its solubility and to make it less irritating. Various other pharmaceutically acceptable acid addition salts of the compounds of formulae I, II and III may likewise be utilized. Such acid addition salts may be derived from a variety of organic and inorganic acids such as sulfuric, phosphoric, p-toluenesulfonic, hydrochloric, hydrobromic, hydroiodic, sulfamic, citric, lactic, maleic, succinic, tartaric, cinnamic, acetic, benzoic, gluconic, ascorbic and related acids. Also, a liquid form could be utilized or, if appropriate, tablets, capsules, etc., may be prepared for oral administration.

The aminoguanidine derivatives encompassed by formula I are conveniently prepared by chemical syntheses well known in the art. Certain of the compounds encompassed by formula I are known compounds readily available from chemical supply houses and/or preparable by synthetic methods specifically published therefor. The novel compounds of formulae III and IV are prepared by analogous routes. For instance, 1,3-diaminoguanidine monohydrochloride and 2-hyrazino- 2-imidazoline hydrobromide are available from Aldrich Chemical Company. Acetic acid hydrazide and L-glutamic acid-gamma-hydrazine hydrate can be obtained from Sigma Chemical Company. Methanesulfonyl hydrazide is obtainable from Lancaster Chemical Co. N-hydroxyhydrazinecarboximidamide tosylate can be synthesized according to the procedure of *J. Med. Chem.*, 27, 236–238 (1984). Likewise, the procedure describing 1-methylhydrazinecarboximidamide tosylate is published in *J. Med. Chem.*, 25, 505–518 (1982). N-(3-dimethylaminopropyl) hydrazinecarboximidamide dihydrobromide hydrate is mentioned in U.S. Pat. No. 4,544,759 (1985).

Other compounds described in the chemical and patent literature and encompassed by formula I are:
N-methylhydrazinecarboximidamide;
N-ethylhydrazinecarboximidamide;
N-propylhydrazinecarboximidamide;
N-butylhydrazinecarboximidamide;
N-hexylhydrazinecarboximidamide;
N,N'-dimethylhydrazinecarboximidamide;
N,N'-diethylhydrazinecarboximidamide;
N,N'-diisopropylhydrazinecarboximidamide;
N-(3-diethylaminopropyl)hydrazinecarboximidamide;
N-(2-diethylaminoethyl)hydrazinecarboximidamide;
N-(2-dimethylaminoethyl)hydrazinecarboximidamide;
N-[2-(4-methylpiperazinyl)ethyl]hydrazinecarboximidamide;
N-[2-(1-pyrrolidinyl)ethyl]hydrazinecarboximidamide;
N-[2-(1-piperidinyl)ethyl]hydrazinecarboximidamide;
N-[2-(1-hexahydroazepinyl)ethyl]hydrazinecarboximidamide;
2-(4-methyl-1-hexahydro-1,4-diazepinyl)propyl]hydrazinecarboximidamide;
N-[2-(1-hexahydroazocinyl)ethyl]hydrazinecarboximidamide;
N-[2-(1-octahydroazoninyl)ethyl]hydrazinecarboximidamide;
N-[2-(2,4-dimethyl-1-pyrrolidinyl)ethyl]hydrazinecarboximidamide;
acetic acid hydrazide;
aspartic acid β-hydrazide;
glutamic acid τ-hydrazide; and
methanesulfonic acid hydrazide.

Parent U.S. Ser. No. 119,958 describes the preparation of the novel compounds of formula III.

The following examples detail the methods and compositions utilizable in the present invention.

EXAMPLE 1

To evaluate the ability of inhibitors of nonenzymatic browning to inhibit tooth straining enhanced by cationic anti-plaque agents, in vitro experiments were performed using bovine serum albumin (BSA; concentration, 25 mg/mL, as the test protein undergoing nonenzymatic browning in the presence of the sugar glucose (at 100 mM).

Aminoguanidine hydrochloride was used as the nonenzymatic browning inhibitor, and chlorhexidine gluconate as the anti-plaque agent known to enhance nonenzymatic browning. The latter was in the form of the prescription mouth rinse Peridex ®, in which it is present at a concentration of 0.12% along with certain other inert ingredients including ethanol (11.6%). The final concentration of chlorhexidine in the experimental mixtures was 0.024%, and 11.6% ethanol was used as a control in all mixtures lacking Peridex ®.

Various incubation mixtures containing combinations of the above components were prepared in a 0.5 M phosphate buffer at pH 7.4 containing 3 mM sodium azide to prevent the growth of microorganisms. The mixtures were left at 37° C. for three weeks, after which time the BSA in each mixture was precipitated by the addition of saturated ammonium sulfate solution. The precipitate was washed in saturated ammonium sulfate solution, and the BSA precipitate dissolved in phosphate-buffered solution. The degree of nonenzymatic browning of each BSA sample was determined by measuring relative fluorescence at an excitation wavelength of 70 nm and an emission wavelength of 440 nm. This is a measure including furoylfuranylimidazole (Pongor et al., *Proceedings of the National Academy of Sciences of the U.S.A.*, 81, pp. 2684–2688 (1984); U.S. Pat. No. 4,665,192). The amount of BSA in the solution was measured by a standard method and the degree of nonenzymatic browning expressed as fluorescence per milligram of protein.

The composition of the incubation mixtures and the resulting specific fluorescence in two experiments is expressed in the following table. Because fluorescence is measured in relative units in each experiment, values in each experiment may be compared directly but not those between experiments.

TABLE 1

| INHIBITION OF NONENZYMATIC BROWNING BY AMINOGUANIDINE | | |
|---|---|---|
| Incubation Mixture | Specific | |
| Fluorescence containing BSA and: | Exp. 1 | Exp. 2 |
| no addition | 8.5 | 1.3 |
| glucose | 36.0 | 10.0 |
| glucose + chlorhexidine | 59.2 | 17.8 |
| glucose + chlorhexidine + 100 mM aminoguanidine | 15.2 | 2.2 |
| glucose + 100 mM aminoguanidine | 15.0 | 1.7 |

It is clear from these results that the incubation of glucose with BSA results in nonenzymatic browning over the control incubation and the inclusion of chlorhexidine significantly increases the degree of browning. This enhanced browning caused by chlorhexidine is as completely inhibited by the inclusion of aminoguanidine as is the browning reacting without chlorhexidine. These same results were obtained by comparing the visible spectra of the BSA solutions. Thus, aminoguanidine inhibits nonenzymatic browning especially the enhanced nonenzymatic browning caused by chlorhexidine.

EXAMPLE 2

To further study the ability of inhibitors of nonenzymatic browning to prevent the discoloration of protein on a surface, such as that which occurs on the tooth surface, the following surface browning experiment was performed. As a substitute for a pellicle-covered tooth surface, unexposed and developed photographic paper was used to provide a fixed protein (gelatin, i.e., collagen) surface on a paper backing. Five millimeter circles were punched and immersed for one week at 50° C. in a solution of 100 mM glucose-6-phosphate in a 0.5 M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or aminoguanidine were included. After incubation, the gelatin/paper disks were rinsed with water, observed for brown color, and photographed.

Figure 1:
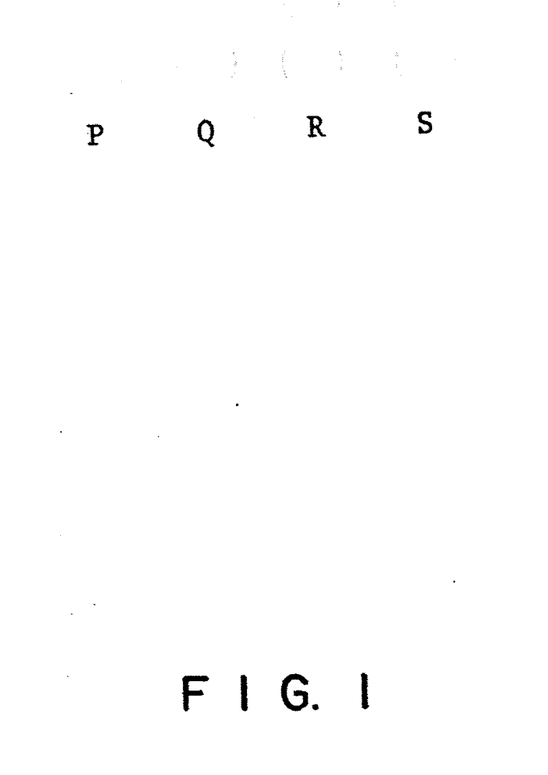
FIG. 1 is a photograph depicting the results of the incubation of gelatin/paper disks with reducing sugars to simulate the environment of a protein-covered tooth surface.

FIG. 1 illustrates the results of one such experiment. Incubation of the disks in glucose-6-phosphate alone (P) showed slight brown color versus disks soaked in buffer alone (not shown). Inclusion of chlorhexidine (in the form of Peridex ® at a final concentration of 0.04% chlorhexidine) showed significant browning (Q). Addition of aminoguanidine hdrochloride (100 mM to the chlorhexidine completely inhibited browning of the gelatin (R), as did inclusion of aminoguanidine in the absence of chlorhexidine (S).

The slight brown color formed by the action of glucose-6-phosphate on the gelatin surface alone and its prevention by aminoguanidine demonstrates the utility of the present invention in preventing nonenzymatic browning of tooth surfaces. The enhanced browning in the presence of chlorhexidine and its complete prevention with aminoguanidine demonstrates the utility of the present invention in preventing the anti-plaque agent enhanced nonenzymatic browning which occurs with chlorhexidine.

EXAMPLE 3

Chlorhexidine is believed to exert its anti-plaque activity by having the ability to stick to the tooth surface and exert anti-microbial activity. The following experiment was performed to ensure that aminoguanidine does not reduce the anti-microbial activity of chlorhexidine.

The KIO strain of Escherichia coli was exposed to tenfold serial dilutions of chlorhexidine (in the form of Peridex ® containing either no addition or a final concentration of 1 mM or 10 mM aminoguanidine hydrochloride. After exposure, bacteria were plated on M63/glucose agar and allowed to grow at 37° C., after which time colonies were counted.

Results showed that aminoguanidine did not reduce the anti-microbial efficiency of chlorhexidine at all dilutions at which inhibition of bacterial growth occurred.

EXAMPLE 4

| Oral Rinse Containing Chlorhexidine and Aminouanidine: | |
| --- | --- |
| Aminoguanidine | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 5

| Toothpaste Containing Aminoguanidine: | |
| --- | --- |
| Aminoguanidine hydrochloride | 5.5% |
| Sorbitol, 70% in water | 25% |
| Sodium saccharin | 0.15% |
| Sodium lauryl sulfate | 1.75% |
| Carbopol 934, 6% dispersion in water | 15% |
| Oil of Spearmint | 1.0% |
| Sodium hydroxide, 50% in water | 0.76% |
| Dibasic calcium phosphate dihydrate | 45% |

| -continued | |
| --- | --- |
| Toothpaste Containing Aminoguanidine: | |
| Water to | 100% |

EXAMPLE 6

The following methods were used to evaluate the compounds of the present invention for their ability to prevent the glucose-mediated cross-linking of protein in vitro. The test protein utilized is bovine serum albumin (BSA) at a concentration of 100 milligrams per milliliter in a 0.5 M sodium phosphate buffer at pH 7.4. Glucose is included in the reaction mixture at a concentration of 200 mM. Sodium azide, 3mM, is included in all solutions to prevent the growth of microorganisms.

To evaluate compounds, they are included in the above reaction mixture at either 1 mM, 10 mM, or 100 mM. An additional set of incubation mixtures also is prepared in the absence of glucose to serve as baseline controls for each inhibitor. A BSA plus glucose mixture in the absence of any inhibitor serves as an indication of the maximum amount of cross-linking that can occur in each mixture.

After incubation of the mixtures for three weeks at 37° C., the BSA in each mixture must be isolated from the other components of the mixture before the degree of browning is determined. This is necessary because many of the inhibitors are either fluorescent themselves or quench the fluorescence of the browned BSA. To effect the separation, the BSA is precipitated by the addition of 1.0 milliliters of saturated ammonium sulfate to each 100 microliters of incubation mixture. The resulting precipitate is centrifuged and the supernatant solutions are discarded. The precipitate is washed once with saturated ammonium sulfate, then the BSA pellet is redissolved in 1 milliliter of phosphate buffered saline (PBS) to give a final protein concentration of about 10 milligrams per milliliter.

The actual protein concentration of the BSA solution is determined by a standard dye-binding protein assay. The fluorescence of the BSA is measured in a spectrofluorimeter at an excitation wavelength of 370 nanometers and an emission wavelength of 440 nanometers. This corresponds to the detection of chromophores including FFI which have formed in the BSA as a formation of advanced glycosylation end products through the reaction of glycosylated amino groups.

The specific fluorescence of the BSA is measured as fluorescence (in arbitrary units) per milligram of BSA. It is expressed as the increase in fluorescence during the incubation period of the sample incubated with glucose minus the corresponding value in the absence of glucose. The degree of inhibition of each compound is expressed in a percentage scale, where 0% represents no inhibition of browning, i.e., the fluorescence developed in an incubation mixture containing only glucose and BSA, in the absence of any inhibitors. One hundred percent inhibition corresponds to the degree of fluorescence developed in the absence of glucose.

Following the above procedure, the following results were obtained using the test compounds at a concentration of 10 mM.

Percent inhibition of browning by various compounds at 10 mM:
85% 1,2,3-triaminoguanidine hydrochloride
84% 1,3-diaminoguanidine monohydrochloride 81% N-hydroxyhydrazinecarboximidamide tosylate
76% 2-hydrazino-2-imidazoline hydrobromide
65% L-glutamic acid-gamma-hydrazide hydrate
63% N,N''-[1,4-piperazinediylbis(3,1-propanediyl)]bishydrazinecarboximidamide tetrahydrobromide
59% N-(3-dimethylaminopropyl)hydrazinecarboximidamide dihydrobromide hydrate
59% N-(3-(4-methylpiperazin-1-yl)propyl)hydrazinecarboximidamide trihydrobromide
53% 1-methylhydrazinecarboximidamide tosylate
49% methanesulfonic acid hydrazide
48% acetic acid hydrazide
45% 1-(2-hydroxyethyl)hydrazinecarboximidamide sulfate 2:1
44% aminoguanidine hemisulfate
43% 1-amino-2-hydrazino-2-imidazoline tosylate
42% N-(2,2-dimethyl-3-dimethylaminopropyl)hydrazinecarboximidamide dihydrobromide
41% N-(3-(4-morpholino)propyl)hydrazinecarboximidamide dihydrobromide
40% aminoguanidine hydrochloride
33% 2-(1-(2-hydroxyethyl)hydrazino)-2-imidazoline sulfate 2:1
32% N-(2-(4-morpholino)ethyl)hydrazinecarboximidamide dihydrobromide
0% no inhibitor

EXAMPLE 7

Evaluation of test compounds at 1 mM was performed the same way as in Example 1. The results are as follows:

42% 2-hydrazino-2-imidazoline hydrobromide
37% N-hydroxyhydrazinecarboximidamide tosylate
37% 1,2,3-triaminoguanidine hydrochloride
37% N,N''-[1,4-piperazinediylbis(3,1-propanediyl)]bishydrazinecarboximidamide tetrahydrobromide
33% 1,2-diamino-2-imidazoline tosylate
31% 1,3-diaminoguanidine monohydrochloride
26% acetic acid hydrazide
24% L-glutamic acid-gamma-hydrazide hydrate
23% N-(3-dimethylaminopropyl)hydrazinecarboximidamide dihydrobromide hydrate
23% N-(3-(4-methylpiperazin-1-yl)propyl)hydrazinecarboximidamide trihydrobromide
22% beta-aspartyl hydrazide
21% 1-(2-hydroxyethyl)hydrazinecarboximidamide sulfate 2:1
21% methanesulfonic acid hydrazide
19% aminoguanidine hydrochloride

EXAMPLE 8

Evaluation of test compounds at 100 mM was performed the same way as in Example 1. The results are as follows:

Percent inhibition of browning by various compounds at 100 mM.
100% N,N''-[1,4-piperazinediylbis(3,1-propanediyl)]bishydrazinecarboximidamide tetrahydrobromide
98% L-glutamic acid-gamma-hydrazide hydrate
98% 1,3-diaminoguanidine monohydrochloride
97% N-(2,2-dimethyl-3-dimethylaminopropyl)hydrazinecarboximidamide dihydrobromide
96% N-hydroxyhydrazinecarboximidamide tosylate
96% N-(3-(4-methylpiperazin-1-yl)propyl)hydrazinecarboximidamide trihydrobromide
95% 2-hydrazino-2-imidazoline hydrobromide
94% aminoguahidine hemisulfate
93% methanesulfonic acid hydrazide
93% N-(3-(4-morpholino)propyl)hydrazinecarboximidamide dihydrobromide
92% N-(3-dimethylaminopropyl)hydrazinecarboximidamide dihydrobromide hydrate
91% aminoguanidine methanesulfonate
90% N-(2-(4-morpholino)ethylhydrazinecarboximidamide dihydrobromide
90% 1-amino-2-hydrazino-2-imidazoline tosylate
88% aminoguanidine hydrochloride
81% 2-(1-(2-hydroxyethyl)hydrazino)-2-imidazoline sulfate 2:1

The in vitro experiments of Examples 6-8 indicate that these agents can be utilized to reduce the pathology associated with the advanced glycosylation of proteins and the formation of crosslinks between proteins and other macromolecules.

EXAMPLE 9

Certain of the novel aminoguanidine derivatives are synthesized in the following manner.

N-(3-(4-morpholino)propyl)hydrazinecarboximidamide dihydrobromide

Hydrazinecarboximidothioic acid ethyl ester hydrobromide (10.0 grams) and 3-(4-morpholino)propylamine (7.56 grams) are dissolved in ethanol (20 milliliters) and kept at room temperature for 2 days, then heated at reflux for 30 minutes. Isopropanol (20 milliliters) is added, and the mixture is cooled and treated with 48% hydrobromic acid (6 milliliters). Additional ethanol (50 milliliters) and isopropanol (20 milliliters) are added and the mixture is stored at −20° C. for two days. The crystalline precipitate is triturated, filtered out and washed with ethanol and isopropanol, giving 14.91 grams of crystalline solid. To purifying this material, 11 grams are dissolved in 16.5 milliliters of water, filtered to remove insoluble material, and diluted with 5.5 milliliters of methanol and 100 milliliters of isopropanol. After storage at room temperature and at 4° C., the precipitate is filtered out and washed with isopropanol, giving 9.0 grams of colorless crystals of the title compound, melting point of 129°–130° C.

Following analogous procedures, the following aminoalkyl hydrazinecarboximidamide derivatives are prepared (substituting for 3-(4-morpholino)propylamine the following reagents):

From 2-(4-morpholino)ethylamine, the compound N-(2-(4-morpholino)ethyl) hydrazinecarboximidamide dihydrobromide, melting point 169°–171° C.

From 3-(4-methylpiperazin-1-yl)propylamine, the compound N-(3-(4-methyl-1-piperazinyl)propyl)hydrazinecarboximidamide trihydrobromide, melting point 212° C.

From 2,2-dimethyl-3-dimethylaminopropylamine, the compound N(2,2-dimethyl-3-dimethylaminopropyl) hydrazine-carboximidamide dihydrobromide, melting point 105°–107° C.

From 1,4-piperazinediylbis(3,1-propylamine), the compound N,N''[1,4-piperazinediylbis(3,1-propanediyl)]bishydrazinecarboximidamide tetrahydrobromide, melting point 241°–244° C.

From 3-dimethylaminopropylamine, the compound N-(3-dimethylaminopropyl)hydrazinecarboximidamide dihydrobromide, melting point 82°–84° C.

EXAMPLE 10

1-(2-hydroxyethyl)hydrazinecarboximidamide sulfate 2:1

Carbimidothioic acid methyl ester sulfate 2:1 (6.955 grams) and -hyroxyethylhydrazine (9.13 grams) are stirred and heated at 40° C. for one hour. Methanol (20 milliliters) is added and the mixture is heated at reflux for four hours. On cooling, crystals separate. Filtration gives 5.34 grams of colorless crystals Three recrystallizations from 88% methanol afford 4.111 grams of the title compound as colorless crystals, melting point 178.5°–180° C.

EXAMPLE 11

2-(1-(2-hydroxyethyl)hydrazino)-2-imidazoline sulfate (2:1)

2-Methylthio-2-imidazoline sulfate (2:1) (1.98 g) and 2-hydroxyethylhydrazine (2.12 g) are heated in ethanol (3 ml) at reflux for 1 hr., then stirred at 25° C. for 3 hr. The solution was diluted with ethanol (20 ml) and kept at 4° C. for 18 hours. The crystals which separated were filtered out and washed with ethanol. Weight 811 mg, mp 190°–4° C.

Similarly, from the corresponding S-methylisothiuronium derivatives are prepared the following compounds or their acid addition salts:

2-1-(2-hydroxyethyl)hydrazino)-3-methyl-1-imidazoline;
2-(1-(2-hydroxyethyl)hydrazino)-4,4-dimethyl-1-imidazoline;
1,3-dimethyl-2-(1-(2-hydroxyethyl)hydrazino)imidazolium;
2-(1-(2-hydroxyethyl)hydrazino)-3,4,5,6-tetrahydropyrimidine;
2-(1-(2-hydroxyethyl)hydrazino)-5,5-dimethyl-3,4,5,6-tetrahydropyrimidine;
2-(1-(2-hydroxyethyl)hydrazino)-5-hydroxy-3,4,5,6-tetrahydropyrimidine;
2-(1-(2-hydroxyethyl)hydrazino)-5,5-dibutyl-3,4,5,6-tetrahydropyrimidine;
2-(1-(2-hydroxyethyl)hydrazino)-3-methyl-3,4,5,6-tetrahydropyrimidine;
1,3-dimethyl-2-(1-(2-hydroxyethyl)hydrazino)-3,4,5,6-tetrahydropyrimidium;
2-(1-(2-hydroxyethyl)hydrazino)-4,5,6,7-tetrahydro-1,3(1H)-diazepine:
2-(1-(2-hydroxyethyl)hydrazino)-4,4,7,7-tetramethyl-4,5,6,7-tetrahydro-1,3(1H)-diazepine:
N-methyl-1-(2-hydroxyethyl)hydrazinecarboximidamide;
N,N'dimethyl-1-(2-hydroxyethyl)hydrazinecarboximidamide; 1-pyrrolidinecarboximidic acid 1-(2-hydroxyethyl)hydrazide;
N-methyl(1-pyrrolidine)carboximidic acid 1-(2-hydroxyethyl)hydrazide;
1-piperidinecarboximidic acid 1-(2-hydroxyethyl)hydrazide;
1-hexahydroazepinecarboximidic acid 1-(2-hydroxyethyl) hydrazide;
1-(4-methylpiperazine)carboximidic acid 1-(2-hydroxyethyl) hydrazide;
1-(4-methylhexahydro-1,4-diazepine)carboximidic acid 1-(2-hydroxyethyl)hydrazide; and
4-morpholinecarboximidic acid 1-(2-hydroxyethyl)hydrazide.

EXAMPLE 12

1,2-Diamino-2-imidazoline p-toluenesulfonate

1-Aminoimidazolidine-2-thione (2.34 g) and methyl p-toluenesulfonate (4.1 g) in ethanol (15 ml) are heated to reflux for 10 minutes, then kept at room temperature for 16 hours. The crystalline precipitate is filtered out and washed with isopropanol to give 4.613 g of 1-amino-2-methylthio-2-midazoline p-toluenesulfonate as colorless needles, of which 3.79 g is placed in methanol (15 ml) and treated with concentrated aqueous ammonia. After stirring for 6 hours, the mixture is diluted with 20 ml isopropanol. After another 12 hours, 5 ml of liquid is distilled off at atmospheric pressure, and 10 ml isopropanol is added to the remainder. The crystals which separate on cooling are filtered out and washed with isopropanol to give 2.323 g of 1,2-diamino-2-imidazoline p-toluenesulfonate, melting point 190°–190.5° C.

EXAMPLE 13

1-Amino-2-hydrazino-2-imidazoline p-toluenesulfonate

1-Amino-2-methylthio-2-imidazoline p-toluenesulfonate (2.123 g) in ethanol (4 ml) was treated with hydrazine (0.67 ml) and stirred at 25° C. for 2 hours. Isopropyl alcohol (6 ml) was added and after stirring for 10 min the crystalline precipitate was filtered out and washed with isopropyl alcohol to give 1.55 g of 1-amino-2-methylthio-2-imidazoline p-toluenesulfonate, melting point 168°–169° C.

EXAMPLE 14

The aminoguanidine derivatives of the present invention are tested according to the method of Stoner, *Agents and Actions,* 17, pp. 5–9 (1985) in order to ascertain their lack of ability to inhibit the enzyme diamine oxidase. This enzyme is responsible for detoxifying histamine and therefore it would be desirable in any therapy to avoid inhibition of this enzyme.

Percent Inhibition at 10 micromolar:
92% Aminoguanidine hydrochloride
0% 1-(2-hydroxyethyl)hydrazinecarboximidamide sulfate 2:1
0% 1-methylhydrazinecarboximidamide tosylate
84% N-hydroxyhydrazinecarboximidamide tosylate
59% 2-hydrazino-2-imidazoline hydrobromide
92% 1,3-diaminoguanidine monohydrochloride
0% N-(3-dimethylaminopropyl)hydrazinecarboximidamide dihydrobromide hydrate
0% N-(3-(4-methylpiperazin-1-yl)propyl)hydrazinecarboximidamide trihydrbbromide
12% N,N''-3,3'-[1,4-piperazinediylbis(3,1propanediyl)-]bishydrazinecarboximidamide tetrahydrobromide
82% 1,2,3-triaminoguanidine hydrochloride
5% N-(3-(4-morpholino)propyl)hydrazinecarboximidamide dihydrobromide
0% N-(2,2-dimethyl-3-dimethylaminopropyl)hydrazinecarboximidamide dihydrobromide
9% 1,2-diamino-2-imidazoline tosylate
9% methanesulfonic acid hydrazide
75% L-glutamic acid-gamma-hydrazide hydrate
32% beta-aspartyl hydrazide
0% acetic acid hydrazide

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of inhibiting the discoloration of teeth resulting from nonenzymatic browning in the oral cavity which comprises administration to a subject in need of such therapy an amount effective to inhibit the formation of advanced glycosylation end products of a composition comprising an agent capable of reacting with the carbonyl moiety of the early glycosylation product formed by the initial glycosylation in the nonenzymatic browning reaction wherein said agent is selected from the group consisting of amino acids and their esters and amides, α-hydrazinophistidine, lysine and the substituted aminoguanidine derivatives having the structural formula wherein R is a group of the formula and $R_1$ is hydrogen or a lower alkyl group of 1-6 carbon atoms, a hydroxyethyl group, or together with $R_2$ is a lower alkylene bridge of 2-4 carbon atoms; $R_2$ is hydrogen or a lower alkyl group of 1-6 carbon atoms or together with $R_1$ or $R_3$ is a lower alkylene bridge of 2-4 carbon atoms, amino, hydroxy, or an aminoalkylene group of the formula wherein n is an integer of 2-7 and $R_6$ and $R_7$ are independently a lower alkyl group of 1-6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring; it may be optionally substituted by a substituent that is identical to the portion of the compound on the first nitrogen of the piperazine ring; $R_3$ is hydrogen, a lower alkyl group of 1-6 carbon atoms, or together with $R_2$ or $R_4$ is a lower alkylene bridge of 2-4 carbon atoms; $R_4$ is hydrogen, a lower alkyl group of 1-6 carbon atoms or together with $R_3$ is a lower alkylene bridge of 2-4 carbon atoms; or an amino group; $R_5$ is hydrogen, or a lower alkyl group of 1-6 carbon atoms; with the proviso that at least one of $R_1$, $R_2$, $R_3$, or $R_5$ is other than a member selected from the group consisting of hydrogen, a lower alkyl group of 1-6 carbon atoms, a hydroxyethyl group, amino, hydroxy and an aminoalkylene group of the formula wherein n is an integer of 2-7 and $R_6$ and $R_7$ are independently a lower alkyl group of 1-6 carbon atoms;

or R is an acyl or a lower alkylsulfonyl group of up to 10 carbon atoms and $R_1$ is hydrogen when R is an acyl or lower alkylsulfonyl group of up to 10 carbon atoms; and their pharmaceutically acceptable acid addition salts, and mixtures thereof together with a pharmaceutically acceptable carrier therefor.

2. The method of claim 1, wherein said agent comprises a compound having an active nitrogen-containing substituent.

3. The method of claim 2, wherein said active nitrogen containing substituent is a hydrazine group.

4. The method of claim 1, wherein said agent is selected from the group consisting of amino acids and their esters and amides.

5. The method of claim 1, wherein said compound is acetic acid hydrazide.

6. The method of claim 1, wherein said compound is aspartic acid β-hydrazide.

7. The method of claim 1, wherein said compound is glutamic acid Γ-hydrazide.

8. The method of claim 1, wherein said compound is methanesulfonic acid hydrazide.

9. The method of claim 1, wherein the composition is formulated as an oral rinse.

10. The method of claim 9, wherein the composition additionally contains an anti-plaque agent.

11. The method of claim 10, wherein the anti-plaque agent is chlorhexidine.

12. The method of claim 1, wherein the composition is formulated as a toothpaste.

13. The method of claim 12, wherein the composition additionally contains an anti-plaque agent.

14. The method of claim 13, wherein the anti-plaque agent is chlorhexidine.

15. The method of claim 1, wherein the composition is formulated for oral administration.

16. The method of claim 1, wherein the composition is formulated for parenteral administration.

17. A method according to claim 1, wherein said agent is of the formula wherein $R_1$ is hydrogen or a lower alkyl group of 1-6 carbon atoms, a hydroxyethyl group, or together with $R_2$ is a lower alkylene bridge of 2-4 carbon atoms; $R_2$ is hydrogen or a lower alkyl group of 1-6 carbon atoms or together with $R_1$ $_{1\, or\, R_2}$ is a lower alkylene bridge of 2-4 carbon atoms, amino, hydroxy, or an aminoalkylene group of the formula wherein n is an integer of 2-7 and $R_6$ and $R_7$ are independently a lower alkyl group of 1-6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring; it may be optionally substituted by a substituent that is identical to the portion of the compound on the first nitrogen of the piperazine ring; $R_3$ is hydrogen, a lower alkyl group of 1-6 carbon atoms, or together with $R_2$ or $R_4$ is a lower alkylene bridge of 2-4 carbon atoms; $R_4$ is hydrogen, a lower alkyl group of 1-6 carbon atoms or together with $R_3$ is a lower alkylene bridge of 2-4 carbon atoms; or an amino group; $R_5$ is hydrogen, or a lower alkyl group of 1-6 carbon atoms; with the proviso that at least one of $R_1$, $R_2$, $R_3$, $R_4$ or $R_5$ is other than a member selected from the group consisting of hydrogen, a lower alkyl group of 1-6 carbon atoms, a hydroxyethyl group, amino, hydroxy, and an aminoalkylene group of the formula wherein n is an integer of 2-7 and $R_6$ and $R_7$ are independently a lower alkyl group of 1-6 carbon atoms; and their pharmaceutically acceptable acid addition salts.

18. A method of claim 17, wherein said compound is 2-hydrazino-2-imidazoline or a pharmaceutically acceptable acid addition salt thereof.

19. A method of claim 17, wherein said compound is 1,2-diamino-2-imidazoline or a pharmaceutically acceptable acid addition salt thereof.

20. A method of claim 17, wherein said compound is 1,-(2hydroxyethyl)hydrazineoarboximidamide or a pharmaceutically acceptable acid addition salt thereof.

21. A method of claim 17, wherein said compound is 2-(1-(2-hydroxyethyl)hydrazino)-2-imidazoline or a pharmaceutically acceptable acid addition salt thereof.

22. A method of claim 17, wherein said compound is N-(2-(4-morpholino)ethyl)hydrazinecarboximidamide or a pharmaceutically acceptable acid addition salt thereof.

23. A method of claim 17, wherein said compound is N-(2-(4morpholino)propyl)hydrazineoarboximidamide or a pharmaceutically acceptable acid addition salt thereof.

24. A method of claim 17, wherein said compound is N-(2,2-dimethyl-3-dimethylaminopropyl)hydrazinecarboximidamide or a pharmaceutically acceptable acid addition salt thereof.

25. A method of claim 17, wherein said compound is N,N''-[1,4-piperazinediylbis(3,1-propanediyl) ]-bishydrazinecarboximidamide or a pharmaceutically acceptable acid addition salt thereof.

26. A method of claim 17, wherein said compound is N-[3-(4-methyl-1-piperazinyl)propyl)hydrazine-carboximidamide or a pharmaceutically acceptable acid addition salt thereof.

* * * * *